US011441121B2

(12) United States Patent
Bennett et al.

(10) Patent No.: US 11,441,121 B2
(45) Date of Patent: *Sep. 13, 2022

(54) SPHEROID CELL CULTURE ARTICLE AND METHODS THEREOF

(71) Applicant: CORNING INCORPORATED, Corning, NY (US)

(72) Inventors: Scott Matthew Bennett, Gray, ME (US); Brian Robb Douglass, Hopkinton, MA (US); Paul Ernest Gagnon, Jr., Wells, ME (US); Gregory Roger Martin, Acton, ME (US); Paul Michael Szlosek, Kennebunk, ME (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/708,473

(22) Filed: Sep. 19, 2017

(65) Prior Publication Data

US 2018/0002660 A1 Jan. 4, 2018

Related U.S. Application Data

(63) Continuation of application No. 14/087,906, filed on Nov. 22, 2013, now Pat. No. 9,790,465.
(Continued)

(51) Int. Cl.
*C12N 5/071* (2010.01)
*C12M 1/00* (2006.01)
(Continued)

(52) U.S. Cl.
CPC .......... *C12N 5/0602* (2013.01); *C12M 23/02* (2013.01); *C12M 23/12* (2013.01); *C12M 23/24* (2013.01); *C12M 25/04* (2013.01); *C12M 29/04* (2013.01)

(58) Field of Classification Search
CPC ....... C12M 23/12; C12M 23/24; C12M 25/04
See application file for complete search history.

(56) References Cited

U.S. PATENT DOCUMENTS 2,947,116 A 8/1960 Earle et al.
3,630,849 A 12/1971 Land et al.
(Continued)

FOREIGN PATENT DOCUMENTS

AU 2004256209 A1 1/2005
CA 2558946 A1 1/2005
(Continued)

OTHER PUBLICATIONS

Tung et al. "High-throughput 3D spheroid culture and drug testing using 384 hanging drop array." Analyst, 2011, 136, 473-478.
(Continued)

*Primary Examiner* — William H. Beisner
(74) *Attorney, Agent, or Firm* — Annie J. Morgan

(57) ABSTRACT

A spheroid cell culture article including:
a frame having a chamber including:
an opaque side wall surface;
a top aperture;
a gas-permeable, transparent bottom; and
optionally a chamber annex surface and second bottom, and at least a portion of the transparent bottom includes at least one concave arcuate surface, is disclosed. Methods of making and using the article are also disclosed.

20 Claims, 9 Drawing Sheets

Related U.S. Application Data

(60) Provisional application No. 61/817,539, filed on Apr. 30, 2013.

(51) Int. Cl.
  *C12M 1/32* (2006.01)
  *C12M 1/04* (2006.01)
  *C12M 1/12* (2006.01)

(56) References Cited

U.S. PATENT DOCUMENTS

| | | |
|---|---|---|
| 4,382,685 A | 5/1983 | Pearson |
| 4,670,396 A | 6/1987 | Bear et al. |
| 4,927,764 A | 5/1990 | Lyman et al. |
| 4,980,293 A * | 12/1990 | Jeffs .................. B01L 3/508 422/561 |
| 5,047,347 A | 9/1991 | Cline |
| 5,151,366 A | 9/1992 | Serkes et al. |
| 5,171,994 A | 12/1992 | Bahraman |
| 5,171,995 A | 12/1992 | Gast et al. |
| 5,240,854 A | 8/1993 | Berry et al. |
| 5,272,084 A | 12/1993 | O'Connell et al. |
| 5,374,557 A | 12/1994 | Verma |
| 5,398,837 A | 3/1995 | Degrassi |
| 5,487,872 A | 1/1996 | Hafeman et al. |
| 5,554,536 A | 9/1996 | Rising |
| 5,598,262 A | 1/1997 | Jutard et al. |
| 5,665,562 A | 9/1997 | Cook |
| 5,693,537 A | 12/1997 | Wilson et al. |
| 5,707,869 A | 1/1998 | Wolf et al. |
| 5,710,043 A | 1/1998 | Pay |
| 5,736,397 A | 4/1998 | Garcia et al. |
| 5,759,494 A | 6/1998 | Szlosek |
| 5,772,905 A | 6/1998 | Chou |
| 5,783,440 A | 7/1998 | Stevens |
| 5,858,309 A | 1/1999 | Mathus et al. |
| 5,972,653 A | 10/1999 | Hillman et al. |
| 5,972,694 A | 10/1999 | Mathus |
| 6,030,829 A | 2/2000 | Dannoux et al. |
| 6,039,972 A | 3/2000 | Barlow et al. |
| 6,306,646 B1 | 10/2001 | Saad et al. |
| 6,348,999 B1 | 2/2002 | Summersgill et al. |
| 6,514,464 B1 | 2/2003 | Knebel |
| 6,521,451 B2 | 2/2003 | Potter |
| 6,567,675 B1 | 5/2003 | Rosen et al. |
| 6,767,607 B2 | 7/2004 | Tanner et al. |
| 6,811,752 B2 | 11/2004 | Barbera-Guillem |
| 6,908,767 B2 | 6/2005 | Bader |
| 7,470,424 B2 | 12/2008 | Kataoka et al. |
| 7,547,547 B2 | 6/2009 | Dang et al. |
| 7,674,346 B2 | 3/2010 | Clements et al. |
| 7,687,262 B2 | 3/2010 | Cattadoris |
| 7,691,369 B2 | 4/2010 | Kataoka et al. |
| 7,727,759 B2 | 6/2010 | Ozawa et al. |
| 7,745,209 B2 | 6/2010 | Martin et al. |
| 7,745,210 B2 | 6/2010 | Martin |
| 7,897,379 B2 | 3/2011 | Kenney et al. |
| 7,919,319 B2 | 4/2011 | Jervis et al. |
| 8,053,230 B2 | 11/2011 | Whittlinger |
| 8,143,053 B2 | 3/2012 | Yerbic |
| 8,148,152 B2 | 4/2012 | Kolossov et al. |
| 8,158,426 B2 | 4/2012 | Wilson et al. |
| 8,158,427 B2 | 4/2012 | Wilson et al. |
| 8,163,537 B2 | 4/2012 | Martin et al. |
| 8,168,432 B2 | 5/2012 | Wilson et al. |
| 8,178,345 B2 | 5/2012 | Bennett et al. |
| 8,273,572 B2 | 9/2012 | Martin et al. |
| 8,318,479 B2 | 11/2012 | Domansky et al. |
| 8,415,144 B2 | 4/2013 | Wilson et al. |
| 8,470,589 B2 | 6/2013 | Martin et al. |
| D685,497 S | 7/2013 | Kenney et al. |
| 8,486,692 B2 | 7/2013 | Simon |
| 8,597,597 B2 | 12/2013 | Deutsch et al. |
| 8,617,879 B2 | 12/2013 | Yu et al. |
| 8,697,443 B2 | 4/2014 | Wilson et al. |
| 8,759,017 B2 | 6/2014 | Owen et al. |
| 8,778,669 B2 | 7/2014 | Lacey et al. |
| 8,846,399 B2 | 9/2014 | Martin et al. |
| 8,906,685 B2 | 12/2014 | Takayama et al. |
| 8,932,544 B2 | 1/2015 | Mueller et al. |
| 9,039,883 B2 | 5/2015 | Guerrieri et al. |
| 9,040,293 B2 | 5/2015 | Gulzow et al. |
| 9,045,721 B2 | 6/2015 | Martin et al. |
| 9,068,281 B2 | 6/2015 | Wu et al. |
| 9,126,199 B2 | 9/2015 | Moritz et al. |
| 9,169,460 B2 | 10/2015 | Cecchi |
| D748,812 S | 2/2016 | Kenney et al. |
| 9,260,684 B1 | 2/2016 | Egeler et al. |
| 9,260,695 B2 | 2/2016 | Crowley et al. |
| 9,493,733 B2 | 11/2016 | Giles |
| 9,494,577 B2 | 11/2016 | Mcgarr et al. |
| 9,573,128 B1 | 2/2017 | McClelland |
| 9,587,213 B2 | 3/2017 | Morgan et al. |
| 9,732,317 B2 | 8/2017 | Wilson |
| 9,790,465 B2 * | 10/2017 | Bennett .............. C12N 5/0602 |
| 9,845,451 B2 | 12/2017 | Martin et al. |
| 9,862,918 B2 | 1/2018 | Ito |
| 10,254,274 B2 | 4/2019 | Miklas et al. |
| 2002/0022219 A1 | 2/2002 | Clements et al. |
| 2002/0172621 A1 | 11/2002 | Barbera-Guillem |
| 2003/0031829 A1 | 2/2003 | Tanner et al. |
| 2003/0104494 A1 | 6/2003 | Ravkin et al. |
| 2003/0183958 A1 | 10/2003 | Goff et al. |
| 2003/0186217 A1 | 10/2003 | Bader |
| 2003/0215941 A1 | 11/2003 | Campbell et al. |
| 2004/0091397 A1 | 5/2004 | Picard |
| 2004/0101955 A1 | 5/2004 | Whitley |
| 2004/0125266 A1 | 7/2004 | Miyauchi et al. |
| 2004/0216835 A1 | 11/2004 | Tanner et al. |
| 2004/0259242 A1 | 12/2004 | Malinge et al. |
| 2005/0032208 A1 | 2/2005 | Oh et al. |
| 2005/0047971 A1 | 3/2005 | Clements et al. |
| 2005/0112030 A1 | 5/2005 | Gaus |
| 2005/0116717 A1 | 6/2005 | Dransfield et al. |
| 2005/0147959 A1 | 7/2005 | Frondoza et al. |
| 2006/0110822 A1 | 5/2006 | Robbins et al. |
| 2006/0234370 A1 | 10/2006 | Korpinen et al. |
| 2006/0252044 A1 | 11/2006 | Okumura et al. |
| 2006/0292654 A1 | 12/2006 | Reardon |
| 2007/0178441 A1 | 8/2007 | Li |
| 2007/0216897 A1 | 9/2007 | Sonda |
| 2008/0003671 A1 | 1/2008 | Martin |
| 2008/0009027 A1 | 1/2008 | Fraker et al. |
| 2008/0118974 A1 | 5/2008 | Martin et al. |
| 2008/0206857 A1 | 8/2008 | Kenney et al. |
| 2008/0297784 A1 | 12/2008 | LeBlanc et al. |
| 2008/0299649 A1 | 12/2008 | Martin et al. |
| 2008/0300278 A1 | 12/2008 | Torrens Jover et al. |
| 2009/0017540 A1 | 1/2009 | Nishio et al. |
| 2009/0018033 A1 | 1/2009 | Morgan et al. |
| 2009/0029462 A1 | 1/2009 | Beardsley et al. |
| 2009/0037293 A1 | 2/2009 | Unger et al. |
| 2009/0170190 A1 | 7/2009 | Nishi et al. |
| 2009/0191620 A1 | 7/2009 | Martin et al. |
| 2009/0288963 A1 | 11/2009 | Guerrieri et al. |
| 2009/0298164 A1 | 12/2009 | Cattadoris et al. |
| 2009/0298166 A1 | 12/2009 | Fang et al. |
| 2010/0055774 A1 | 3/2010 | Wilson |
| 2010/0068793 A1 | 3/2010 | Ungrin et al. |
| 2010/0093075 A1 | 4/2010 | Muller |
| 2010/0112014 A1 | 5/2010 | Gilbert et al. |
| 2010/0112684 A1 | 5/2010 | Lee et al. |
| 2010/0119418 A1 | 5/2010 | Clements et al. |
| 2010/0170790 A1 | 7/2010 | Takahashi et al. |
| 2010/0190197 A1 | 7/2010 | Martin et al. |
| 2010/0197013 A1 | 8/2010 | Kamp et al. |
| 2010/0247386 A1 | 9/2010 | Deutsch et al. |
| 2010/0273258 A1 | 10/2010 | Lannutti et al. |
| 2010/0297600 A1 | 11/2010 | Cecchi |
| 2011/0086375 A1 | 4/2011 | Ungrin et al. |
| 2011/0097790 A1 | 4/2011 | Yerbic |
| 2011/0129923 A1 | 6/2011 | Wilson et al. |
| 2011/0229961 A1 | 9/2011 | Higashi et al. |
| 2012/0064627 A1 | 3/2012 | Khine et al. |

(56) References Cited

U.S. PATENT DOCUMENTS

| | | |
|---|---|---|
| 2012/0129208 A1 | 5/2012 | Khine et al. |
| 2012/0129257 A1 | 5/2012 | Yu et al. |
| 2012/0219572 A1 | 8/2012 | Prockop et al. |
| 2013/0122539 A1 | 5/2013 | Li et al. |
| 2013/0122580 A1 | 5/2013 | Tsukada et al. |
| 2013/0143254 A1 | 6/2013 | Thomas et al. |
| 2013/0164848 A1 | 6/2013 | Munaka et al. |
| 2013/0203159 A1 | 8/2013 | Itoh et al. |
| 2013/0344598 A1 | 12/2013 | Nistor |
| 2014/0027784 A1 | 1/2014 | Wada et al. |
| 2014/0099717 A1 | 4/2014 | Fraker et al. |
| 2014/0106394 A1 | 4/2014 | Ko et al. |
| 2014/0106452 A1 | 4/2014 | Vukasinovic |
| 2014/0120573 A1 | 5/2014 | Tavana et al. |
| 2014/0178992 A1 | 6/2014 | Nakashima et al. |
| 2014/0221225 A1 | 8/2014 | Danen et al. |
| 2014/0226004 A1 | 8/2014 | Son et al. |
| 2014/0227784 A1 | 8/2014 | Ejiri et al. |
| 2014/0315296 A1 | 10/2014 | Wilson |
| 2014/0322806 A1 | 10/2014 | Bennett et al. |
| 2015/0004686 A1 | 1/2015 | Goral et al. |
| 2015/0064738 A1 | 3/2015 | Tsukada et al. |
| 2015/0072405 A1 | 3/2015 | Ito |
| 2015/0184119 A1 | 7/2015 | Tsukada et al. |
| 2015/0247112 A1 | 9/2015 | Orr et al. |
| 2016/0003796 A1 | 1/2016 | Kranbuehl |
| 2016/0017267 A1 | 1/2016 | Hansen et al. |
| 2016/0040120 A1 | 2/2016 | Gottwald et al. |
| 2016/0137962 A1 | 5/2016 | Ejiri et al. |
| 2016/0194588 A1 | 7/2016 | Guenat et al. |
| 2016/0216250 A1 | 7/2016 | Ritter et al. |
| 2017/0067019 A1 | 3/2017 | Ho |
| 2017/0073625 A1 | 3/2017 | Kasuto et al. |
| 2017/0226455 A1 | 8/2017 | Fang et al. |
| 2017/0283757 A1 | 10/2017 | Carter et al. |
| 2017/0306281 A1 | 10/2017 | Martin et al. |
| 2017/0342363 A1 | 11/2017 | Fang et al. |
| 2018/0201888 A1 | 7/2018 | Miwa et al. |
| 2020/0239854 A1 | 7/2020 | Ayano et al. |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1234112 A | 11/1999 |
| CN | 1875093 A | 12/2006 |
| CN | 201626959 A | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| DE | 8309876 U1 | 12/1983 |
| DE | 10019862 A1 | 11/2001 |
| DE | 202006017853 U1 | 2/2007 |
| DE | 102009005526 A1 | 7/2010 |
| DE | 102014214077 A1 | 1/2016 |
| DE | 102014017728 A1 | 6/2016 |
| EP | 0307048 A2 | 3/1989 |
| EP | 0605527 A1 | 7/1994 |
| EP | 0681846 A2 | 11/1995 |
| EP | 0800571 A2 | 10/1997 |
| EP | 0834552 A1 | 4/1998 |
| EP | 965633 A1 | 12/1999 |
| EP | 1181349 A1 | 2/2002 |
| EP | 1445022 B1 | 10/2006 |
| EP | 1348533 B1 | 11/2006 |
| EP | 1988152 A1 | 11/2008 |
| EP | 2032262 A2 | 3/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 | 10/2016 |
| EP | 3296018 A1 | 3/2018 |
| EP | 3351615 A1 | 7/2018 |
| EP | 3372666 A1 | 9/2018 |
| GB | 2147100 A | 5/1985 |
| JP | 06-038734 A | 2/1994 |
| JP | 06327462 A | 11/1994 |
| JP | 09173049 A | 7/1997 |
| JP | 09-234811 A | 9/1997 |
| JP | 10210866 A | 8/1998 |
| JP | 10210966 A | 8/1998 |
| JP | 2001-106749 A | 4/2001 |
| JP | 2003135056 A | 5/2003 |
| JP | 2003180335 A | 7/2003 |
| JP | 2004129558 A | 4/2004 |
| JP | 2006-121991 A | 5/2006 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009050194 A | 3/2009 |
| JP | 2009-183288 A | 8/2009 |
| JP | 2009-542230 A | 12/2009 |
| JP | 2010088347 A | 4/2010 |
| JP | 2010104327 A | 5/2010 |
| JP | 2010-518879 A | 6/2010 |
| JP | 2010158214 A | 7/2010 |
| JP | 2011-509686 A | 3/2011 |
| JP | 2011-521642 A | 7/2011 |
| JP | 2011172533 A | 9/2011 |
| JP | 2011-528226 A | 11/2011 |
| JP | 2012249547 A | 12/2012 |
| JP | 2013055911 A | 3/2013 |
| JP | 2014132869 A | 7/2014 |
| JP | 2015012827 A | 1/2015 |
| JP | 2015-029431 A | 2/2015 |
| JP | 2015073520 A | 4/2015 |
| JP | 5845185 B2 | 1/2016 |
| JP | 2016-136920 A | 8/2016 |
| JP | 2016136921 A | 8/2016 |
| JP | 2017-532970 A | 11/2017 |
| JP | 2018-108032 A | 7/2018 |
| KR | 1020140113139 A | 9/2014 |
| KR | 10-2014-0125662 A | 10/2014 |
| WO | 1992007063 A2 | 4/1992 |
| WO | 93/07258 A1 | 4/1993 |
| WO | 96/21851 A2 | 7/1996 |
| WO | 9815355 A2 | 4/1998 |
| WO | 1998031466 A1 | 7/1998 |
| WO | 2001080997 A1 | 11/2001 |
| WO | 2001092462 A1 | 12/2001 |
| WO | 2004/044120 A2 | 5/2004 |
| WO | 2004/094060 A1 | 11/2004 |
| WO | 2005047464 A2 | 5/2005 |
| WO | 2006043267 A1 | 4/2006 |
| WO | 2007/015770 A1 | 2/2007 |
| WO | 2007097120 A1 | 8/2007 |
| WO | 2008/006104 A2 | 1/2008 |
| WO | 2008/008149 A1 | 1/2008 |
| WO | 2008/106771 A1 | 9/2008 |
| WO | 2008118500 A1 | 10/2008 |
| WO | 2008/140295 A1 | 11/2008 |
| WO | 2008/149039 A2 | 12/2008 |
| WO | 2008153783 A1 | 12/2008 |
| WO | 2009094125 A2 | 7/2009 |
| WO | 2009148509 A1 | 12/2009 |

(56) References Cited

FOREIGN PATENT DOCUMENTS

| | | |
|---|---|---|
| WO | 2009148512 A2 | 12/2009 |
| WO | 2010008566 A2 | 1/2010 |
| WO | 2010/069589 A1 | 6/2010 |
| WO | 2012036011 A1 | 3/2012 |
| WO | 2012/077683 A1 | 6/2012 |
| WO | WO-2012170232 A1 * 12/2012 ........... C12N 5/0068 |
| WO | 2013042360 A1 | 3/2013 |
| WO | 2013/108293 A1 | 7/2013 |
| WO | 2013/116449 A1 | 8/2013 |
| WO | 2014/042162 A1 | 3/2014 |
| WO | 2014072432 A1 | 5/2014 |
| WO | 2014/140181 A1 | 9/2014 |
| WO | 2014156455 A1 | 10/2014 |
| WO | 2014165273 A1 | 10/2014 |
| WO | 2014171782 A1 | 10/2014 |
| WO | 2014/179196 A1 | 11/2014 |
| WO | 2014196204 A1 | 12/2014 |
| WO | 2015033507 A1 | 3/2015 |
| WO | 2015/061907 A1 | 5/2015 |
| WO | 2016064757 A1 | 4/2016 |
| WO | 2016069885 A1 | 5/2016 |
| WO | 2016069892 A1 | 5/2016 |
| WO | 2016069895 A1 | 5/2016 |
| WO | 2016069917 A1 | 5/2016 |
| WO | 2016069930 | 5/2016 |
| WO | 2017025584 A1 | 2/2017 |
| WO | 2017/047735 A1 | 3/2017 |
| WO | 2017/077163 A1 | 5/2017 |
| WO | 2017142410 A1 | 8/2017 |
| WO | 2018200893 A1 | 11/2018 |
| WO | 2019014621 A1 | 1/2019 |
| WO | 2019014627 A1 | 1/2019 |
| WO | 2019014635 A1 | 1/2019 |
| WO | 2019014636 A1 | 1/2019 |
| WO | 2019178039 A1 | 9/2019 |

OTHER PUBLICATIONS

Uchida et al; "An Injectable Spheroid System With Genetic Modification for Cell Transplantation Therapy"; Biomaterials, 35 (2014) 2499-2506.
Urich et al; "Multicellular Self-Assembled Spheroidal Model of the Blood Brain Barrier"; Scientific Reports, 3, 1500, 8 Pages.
Vinci et al. Advances in establishment and analysis of three-dimensional tumor spheroid-based functional assays for target validation and drug evaluation, BMC Biology 2012, 10:29.
Weegman et al; "Nutrient Regulation by Continuous Feeding Removes Limitation on Cell Yeild in the Large-Scale Expansion of Mamalian Cell Spheroids"; PLOS One; Oct. 2013, vol. 8, Issue 10, 10 Pages.
Xu et al. "Characterization of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003;189:100-11.
Yamada et al. "Efficient induction of hepatocyte spheroids in a suspension culture using a water-soluble synthetic polymer as an artificial matrix." J Biochem 1998;123: 1017-23.
Achilli; "Advances in the Formation, Use and Understanding of Muli-Cellular Spheroids", Expert Opin. Biol. Ther. (2012) 12 (10) 1347-1360.
Alepee et al. "State of the art 3D cultures (organs-on-a-chip) in safety testing and pathophysiology" Trnasatlantic Think Tank for Toxicology, t4 Workshop Report, Altex 31 4/14, pp. 441-477, retrieved from: http://dx.doi.org/10.14573/altex1406111 (Jul. 14, 2014).
Anada et al; "An Oxygen-Permeable Spheroid Culture System for the Prevention of Central Hypoxia and Necrosis of Spheroids"; Biomaterials, 33, (2012) 8430-8441.
Bartosh et al; "Aggregation of Human Mesenchymal Stromal Cells (MSCS) Into 3D Spheroid Enhances Their Antiinflammatory Properties"; PNAS, Aug. 3, 2010, vol. 107, No. 31 pp. 13724-13729.
Carver et al; "Multicellular Tumor Spheroids as a Model for Assessing Delivery of Oligonucleotides in Three Dimensions"; Molecular Therapy-Nucleic Acids (2014) 3, E153; 8 Pages.
Chen et al. "Microfluidic array for 3-dimensional perfusion culture of human mammary epithelial cells", Biomedical Microdevices (2011) vol. 13, issue 4. p. 753-758.
Choi et al., "Feasibility of a simple double-layered coculture system incorporating metabolic processes of the intestine and liver tissue: application to the analysis of benzo[a]pyrene toxicity" Toxicology in Vitro, vol. 18, pp. 393-402, 2004.
Dolznig and Walzl, "Organotypic spheroid cultures to study tumor-stroma interactions during cancer development." Drug discovery today, V 8., No. 2-3, 2011, 113-118.
Engelberg and Ropella, "Essential operating principles for tumor spheroid growth." BMC Systems Biology 2008, 2, 110.
Friedrich et al. "Spheroid-based drug screen: considerations and practical approach." Nature protocols, 2009, vol. 4 No. 3, 309-323.
Friedrich et al: "Experimental anti-tumor therapy in 3-D: spheroids—old hat or new challenge?" Int J Radiat Biol 2007, 83:849-871.
Frith et al. "Dynamic three-dimensional culture methods enhance mesenchymal stem cell properties and increase therapeutic potential." Tissue engineering, 2010, 16, No. 4, 735-749.
Fukuda Et al. "Efficacy of a polyurethane foam/spheroid artificial liver using human hepatoblastoma cell line (HepG2)." Cell Transplant 2003;12:51-8.
G-Plate: Accelerate your cell cultures to the next dimension, "An original cell culture model allowing for inland shaped 3D cell aggregates" 1 page, retrieved Sep. 8, 2015.
Haycock. "3D cell culture: a review of current approaches and techniques." Methods Mol Biol. 2011;695:1-15.
Hirschhaeuser et al., "Mulicellular tumor spheroids: An underestimated tool is catching up again." Journal of Biotechnology, 2010, 148, 3-15.
Howes et al; "3-Dimensional Culture Systems for Anit-Cancer Compound Profiling and High-Throughput Screening Reveal Increases in EGFR Inhibitor-Mediated Cytotoxicity Compared to Monolayer Culture Systems"; PLOS One; Sep. 2004, vol. 9, Issue 9, 11 Pages.
Hribar et al; "Nonlinear 3D Projection Printing of Concave Hydrogel Microstructures for Long-Term Multicellular Spheroid and Embryoid Body Culture"; Lab Chip, 2015, 15, 2412-2418.
Hwang et al; "Microwell-Mediated Control of Embryoid Body Size Regulates Embryonic Stem Cell Fate via Differential Expression of WNT5A and WNT11"; PNAS; Oct. 6, 2009, vol. 106, No. 40, pp. 16978-16983.
International Search Report and Written Opinion PCT/US2014/035635 dated Aug. 22, 2014.
Kelm et al. "Method for generation of homogeneous multicellular tumor spheroids applicable to a wide variety of cell types." Biotechnol Bioeng 2003;83:173-80.
Koide et al. "Formation of multicellular spheroids composed of adult rat hepatocytes in dish with positively charged surfaces and under other nonadherent environments." Exp Cell Res 1990;186: 227-35.
Kunz-Schughart et al: "The use of 3-D cultures for high-throughput screening: the multicellular spheroid model." J Biomol Screen 2004, 9:273-285.
Kutsuzawa et al; "Highly Robust Protein Production by Co-Culture of Cho Spheroids Layared on Feeder Cells in Serum-Free Medium"; Colloid Polym Sci (2014) 292; 839-848.
Labusca et al. "Scaffold-free culture of mesenchymal stem cell spheroids in suspension preserves multilineage potential", Cell Tissue Res. Mar. 2012 ; 347(3): 701-711.
Landry et al. "Spheroidal aggregate culture of rat liver cell: histotypic reorganization, biomatrix deposition, and maintenance of functional activities." J Cell Biol 1985;101:914-23.
Lau et al., "Evaluation of a Novel In Vitro CACO-2 Hepatocyte Hybrid System for Predicting In Vivo Oral Bioavailability" Drug Metabolism and Disposition, vol. 32, No. 9, pp. 937-942, 2004.
Liu et al. "Quasi-spherical microwells on superhydrophobic substrates for long term culture of multicellular spheroids and high throughput assays" Biomaterials and Cancer 35 (2014) pp. 6060-6068.

(56) References Cited

OTHER PUBLICATIONS

Liu et al; "Advanced Micromachining of Concave Microwells for Long Term On-Chip Culture of Multicellular Tumour Spheroids", ACS Appl. Mater. Interfaces, 2014, 35 Pages.

Lu et al. "Galactosylated PVDF membrane promotes hepatocyte attachment and functional maintenance." Biomaterials 2003;24:4893-903.

Madoux et al; "Building Phenotypic 3D Spheroid HTS Assays to Identify Synthetic Lethal Small Molecule Inhibitors of KRAS"; The Scripps Research Institute Molecular Screening Center and Department of Cancer Biology, Scripps Florida, Jupiter, Florida, Department of Pathology, Jupiter Medical Center, Jupiter, Florida.

Markovitz-Bishitz, "A polymer microstructure array for the formation, culturing, and high throughput drug screening of breast cancer spheroids" Biomaterials and Biotechnology 31 (2010) pp. 8436-8444.

Messner et al., Multi-cell type human liver microtissues for hepatotoxicity testing. Archives of Toxicology Nov. 11, 2012.

Mironov et al; "Organ Printing: Tissue Spheroids as Buliding Blocks" Biomaterials, 2009; 30 (12) 2164-2174.

Moon et al; "Optimizing Human Embryonic Stem Cells Differentiation Efficiency by Screening Size-Tunable Homogenous Embryoid Bodies"; Biomaterials; 35 (2014) 5987-5997.

Murphy et al; "3D Bioprinting of Tissues and Organs"; Nature Biotechnology, vol. 32, No. 8, Aug. 2014, pp. 773-785.

Otsuka et al. "Two-dimensional multiarray formation of hepatocyte spheroids on a microfabricated PEG-brush surface." Chembiochem 2004;5:850-5.

Peshwa et al. "Mechanistics of formation and ultrastructural evaluation of hepatocyte spheroids." In Vitro Cell Dev Biol Anim 1996;32:197-203.

Rezende et al; Scalable Biofabrication of Tissue Spheroids for Organ Printing; Sciverse Science Direct, Porcedia Cirp 5, (2013) 276-281.

Sa et al. "Round-bottomed Honeycomb Microwells: Embryoid body shape correlates with stem cell fate" Journal of Developmental Biology and Tissue Engineering vol. 4(2), pp. 12-22, May 2012.

Sakai et al. "Large-scale preparation and function of porcine hepatocyte spheroids." Int J Artif Organs 1996;19:294-301.

Sakai et al; "Detachably Assembled Microfluidic Device for Perfusion Culture and Post-Culture Analysis of Spheroid Array"; Biotechnol. J. 2014, 9, 971-979.

Sakai et al; "Technique for the Control of Spheroid Diameter Using Microfabricated Chips"; Sciencedirect, ACTA Biomaterials 3 (2007) 1033-1040.

Sart et al. "Three-dimensional aggregates of mesenchymal stem cells: cellular mechanisms, biological properties and applications." Tissue engineering, 2013, Part B, 00, No. 00, 1-16.

Seldon et al; "Evaluation of Encapsulated Liver Cell Spheroids in a Fluidised-Bed Bioartificial Liver for Treatment of Ischaemic Acute Liver Failure in Pigs in the Translational Setting"; PLOS One; Dec. 2013, vol. 8, Issue 12, 12 Pages.

Stemcell Technologies, Reproducible and Uniform Embryoid Bodies Using AggreWell Plates, StemCell Technologies, Version 3.0.0, Mar. 2011, Catalog #29146, pp. 1-28.

Takezawa et al. "Morphological and immunocytochemical characterization of a heterospheroid composed of fibroblasts and hepatocytes." J Cell Sci 1992;101:495-501.

Tobe et al. "Receptor-mediated formation of multilayer aggregation of primary rat hepatocytes on lactose-substituted polystyrene." Biochem Biophys Res Commun 1992;184:225-30.

Tong et al. "Long-term culture of adult rat hepatocyte spheroids." Exp Cell Res 1992;200:326-32.

Truckemüller, et al., Thermoforming of Film-Based Biomedical Microdevices, Adv. Mater. 2011, 23, pp. 1311-1329.

Endo et al., Drug Deliv. and Transl. Res., 2012, vol. 2, p. 398-405.

AxoSIM, Nerve-On-A-Chip Mini-Brain About Team; 6 Pages; (Downloaded Mar. 9, 2020); http://axosim.com/.

Corning Life Sciences Product Portfolio; 5 Pages Saved Mar. 6, 2020.

Aline; "We Engineer Microfluidic Products"; 7 Pages; (2020) https://alineinc.com/.

BIOIVT Elecativing Science®; 6 Pages; (2020); http://www.hepregen.com/.

Cheng et al; "MICRORNA-34a Targets Forkhead Box j2 to Modulate Differentiation of Endothelial Progenitor Cells in Response to Shear Stress" J Mol Cell Cardiol. Sep. 2014;74:4-12.

CN-Bio; "Transforming Drug Discovery and the Lives of Patients"; 5 Pages; (2020) http://cn-bio.com/.

Colazzo et al; "Shear Stress and VEGF Enhance Endothelial Differentiation of Human Adipose-Derived Stem Cells" Growth Factors, Oct. 2014;32(5):139-49.

Corning® HTS Transwell®-96 Tissue Culture Systems, Permeable Supports for High Throughput Screening Applications; 2 Pages (2004).

Tissue Dynamics, "Disruptive Drug Development"; 3 Pages; (Downloaded Mar. 9, 2020); https://www.tissuedynamics.com/.

Domansky et al; "Perfused Multiwell Plate for 3D Liver Tissue Engineering" Lab Chip, 2010, 10:51-58.

Emulate; 6 Pages; (2019) https://emulatebio.com/.

Tissuse, "Emulating Human Biology, Pioneering Human-On-A-Chip Developments"; 1 Page; (Downloaded Mar. 9, 2020) https://www.tissuse.com/en/.

GeoCHEM Incorporated; Product Line; https://www.geocheminc.com, 4 Pages; (2020).

Hµrel® Corporation, Bioanalytic Tools Company; 2 Pages; (2013); http://hurelcorp.com/.

Jeon et al; "Combined Effects of Flow-Induced Shear Stress and Micropatterned Surface Morphology on Neuronal Differentiation of Human Mesenchymal Stem Cells" J Biosci Bioeng Feb. 2014;117(2):242-247.

Jiang et al; "Shear Enhances Thrombopoiesis and Formation of Microparticles That Induce Megakaryocytic Differentiation of Stem Cells", Blood, Sep. 25, 2014;124(13):2094-2103.

Kim et al; "Shear Stress Induced by an Interstitial Level of Slow Flow Increases the Osteogenic Differentiation of Mesenchymal Stem Cells Through TAZ Activation" PLoS One. Mar. 21, 2014;9(3), e92427, 9 pages.

Liquid Surge Control, LLC; "The Latest in Drop-In Baffle Technology"; 2 Pages; (2019).

Elveflow; "Microfluidics Innovation Center"; 6 Pages; (Downloaded Mar. 9, 2020); https://www.elveflow.com/.

Nortis; "Bridging the Gap Between In Vitro and In Vivo Research"; 16 Pages; (2015); https://www.nortisbio.com/.

Mimetas the Organ-On-A-Chip Company; "Organ-On-A-Chip Models for Science and Pharma"; 4 Pages; (Downloaded Mar. 9, 2020); https://mimetas.com/.

Organovo, Pioneering Bioprinted Tissues to Treat Disease "; 2 Pages; (Downloaded Mar. 9, 2020) http://organovo.com/".

Satoh et al; "A Pneumatic Pressure-Driven Multi-Throughput Microfluidic Circulation Culture System" Lab Chip, 2016, 16, 2339-2348.

Tara; "Innovating Predictive Cardiac Physiology"; 4 Pages; (2019) http://tarabiosystems.com/.

The Lab Depot® Products for Discovery Lab Supplies; Shake Flasks, 3 and 4 Baffles Product Information; 5 Pages (2019).

Wikipedia; "Antiroll Tanks"; 3 Pages; Page Last Edited May 23, 2019.

Wrighton et al; "Forces of Change: Mechanics Underlying Formation of Functional 3D Organ Buds" Cell Stem Cell, May 7, 2015; 16(5): 453-454.

European Patent Application No. 14727673.7; Communication pursuant to Article 94(3) EPC dated Aug. 6, 2018; 5 pages; European Patent Office.

International Search Report and Written Opinion of the International Searching Authority; PCT/US14/35635; dated Aug. 22, 2014; 9 Pages; European Patent Office.

Labusca, "Scaffold free 3D culture of mesenchymal stem cells; implications for regenerative medicine", J Transplant Stem Cel Biol 2015 2(1): 8.

Lovett et al. "Vascularization Strategies for Tissue Engineering" Tissue Engineering Part B, 2009, vol. 15, No. 3, pp. 353-370.

(56) References Cited

OTHER PUBLICATIONS

Brandrup et al., "Polymer Handbook", Fourth Edition, Wiley-Interscience Publication,, Permeability and diffusion data, 1999, 9 pages (Contributors; Preface).
Hsiao et al., "Effects of 3D Microwell Culture on Initial Fate Specification in Human Embryonic Stem Cells", Published in final edited form as AIChE J. Vol. 60 No.4, Apr. 2014, pp. 1225-1235.
Japanese Patent Application No. 2020-502649, Office Action dated Apr. 20, 2022, 10 pages (4 pages of English Translation and 6 pages of Original Document), Japanese Patent Office.
Junji Fukuda et al., "Hepatocyte Spheroid Arrays Inside Microwells Connected With Microchannels", Biomicrofluidics 5, 2011, pp. 10.
LONZA Inc., "SeaPrep Agarose: An Ultralow Gelling, Soft Agarose", Available Online at Khttp://www.lonzabio.jp/catalog/pdf/pd/PD031.pdf>, 2007, pp. 1-4.
Martin et al., "Agarose And Methylcellulose Hydrogel Blends For Nerve Regeneration Applications", J. Neural Eng., vol. 5, 2008, pp. 221-231.
Polyimide: Japan Polyimide and Aromatic Polymers Study Group, 2010, pp. 364-371 Table 2.
Yang et al. ,"An Agarose-Gel Based Method for Transporting Cell Lines", Current Chemical Genomics, vol. 3, Jan. 2009, pp. 50-53.
Zuidema et al., "Fabrication And Characterization Of Tunable Polysaccharide Hydrogel Blends For Neural Repair", Acta Biomaterialia, vol. 7, No. 4, Apr. 2011, pp. 1634-1643.

\* cited by examiner

SPHEROID CELL CULTURE ARTICLE AND METHODS THEREOF

CROSS-REFERENCE TO RELATED APPLICATIONS

This application is filed under 35 U.S.C. § 111 as a continuation application of U.S. patent application Ser. No. 14/087,906, filed on Nov. 22, 2013, which claims the benefit of priority to U.S. Provisional Application No. 61/817,539 filed on Apr. 30, 2013, the content of which is relied upon and incorporated herein by reference in its entity.

The entire disclosure of any publication or patent document mentioned herein is incorporated by reference.

BACKGROUND

The disclosure generally relates to a cell culture well article and methods of making and using the article

SUMMARY

In embodiments, the disclosure provides a well article for culturing and assaying, for example, spheroidal cell masses. The well article includes at least one chamber having an opaque side wall; a transparent, round or concave bottom surface; and the transparent bottom is gas-permeable.

In embodiments, the disclosure provides methods for making the well article, and methods of using the well article in spheroid cell culture or in cellular assays.

In embodiments, the disclosure also provides a multi-well plate article having wells or chambers with opaque walls and a gas-permeable, transparent round-bottom, and methods for making the round-bottom multi-well plate article. The transparent round-bottom, such as an optically clear bottom window, permits convenient microscopic visualization or examination of the cultured spheroid cell mass.

In embodiments, the disclosure provides a well plate having a base, the base having a conical or tapered geometry, such as a forty five degree (45°) angle, or like taper angles, from the sidewall to a radius at the apex (i.e., the very bottom of the well) to provide a round-bottom well or multiwell plate having an opaque sidewall and an optically clear window or base for optical visualization, such as with a microscopic or like devices, of a spheroid cell culture.

BRIEF DESCRIPTION OF THE DRAWINGS

In embodiments of the disclosure.

DETAILED DESCRIPTION

Figure 1:
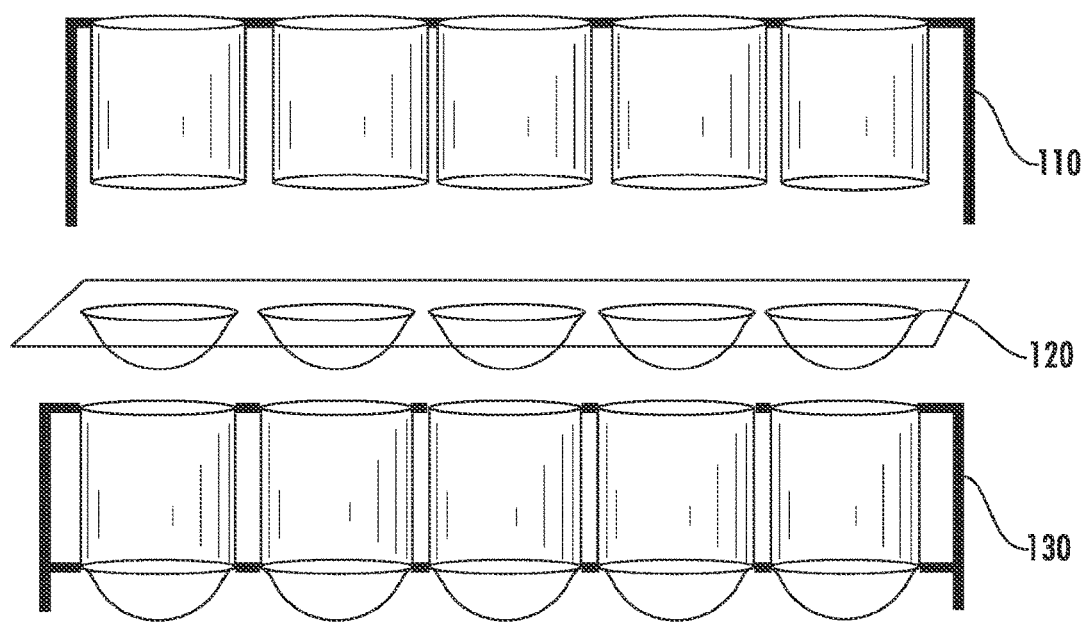
FIG. 1 schematically shows methods for joining pre-formed or molded components to make examples of the disclosed articles.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed apparatus and the disclosed method of making and using the apparatus provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event, circumstance, or structure, can or cannot occur, and that the description includes instances where the event, circumstance, or structure, occurs and instances where it does not.

"Consisting essentially of" or "consisting of" in embodiments can refer to, for example:

a spheroid cell culture article having:
    a frame having a chamber or a plurality of chambers, for example, a well, each chamber having:
    an opaque side wall surface, such as a well having an opaque side wall;
    a top aperture for operational access to the chamber;
    a gas-permeable, transparent bottom surface; and optionally a porous membrane insert in at least one of the chambers, at least a portion of the transparent bottom includes at least one concave arcuate surface, or a plurality of concave arcuate surfaces within a single chamber;

a method of making the abovementioned spheroid cell culture article including:

combining the gas-permeable, transparent arcuate bottom surface portion and an opaque side wall surface portion to form the article, wherein the combining is accomplished with any of the methods disclosed herein or any other suitable methods; and optionally inserting a porous membrane liner in at least one of the chambers; and a method of using the article for culturing spheroids including:

charging the disclosed spheroid cell culture article with culture media; and adding spheroid forming cells to the culture media, as defined herein.

The article, the method of making the article, and the method of using the article, of the disclosure can include the components or steps listed in the claim, plus other components or steps that do not materially affect the basic and novel properties of the compositions, articles, apparatus, or methods of making and use of the disclosure, such as a particular article configuration, particular additives or ingredients, a particular agent, a particular structural material or component, a particular irradiation or temperature condition, or like structure, material, or process variable selected.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, and like aspects, and ranges thereof, are for illustration only; they do not exclude other defined values or other values within defined ranges. The apparatus and methods of the disclosure can include any value or any combination of the values, specific values, more specific values, and preferred values described herein, including explicit or implicit intermediate values and ranges.

The formation of uniformly-sized spheroids of, for example, tumor cells, can be facilitated if the cells are cultured in a round-bottom vessel that has low-adhesion properties. Researchers from the Institute of Cancer Research in Sutton, UK, used Corning, Inc.'s, ultra-low-adhesion (ULA)-coated 96-well clear, round-bottom, polystyrene microplates to produce tumor spheroids that enabled target validation and drug evaluation (see Vinci et al., *BMC Biology*, 2012, 10:29). The spheroids enhanced the biological relevance of the tumor cell cultures and facilitated a range of functional assays. The round-bottom well shape along with gravity and the ultra-low attachment coat or coating, encouraged the cells to come together and self-assemble into the spheroid shape rather than to form a monolayer of cells.

While the clear, round-bottom, ULA-coated wells of the 96-well plate were utilized with good results for migration and invasion assays due to the optical clarity of the structural polymer, evaluation of anti-cancer agents using fluorescent or luminescent detection in this plate were less optimal since the clear sidewalls added to the noise in the detected signal. While the tumor cells could be moved into opaque 96-well plates, this calls for pipetting the spheroids, which can be delicate, difficult, and time-consuming.

In embodiments, the present disclosure provides a spheroid cell culture article comprising:

a frame having a chamber, for example, a well, comprising:

an opaque side wall surface;

a top aperture; and a gas-permeable, transparent bottom surface, and at least a portion of the bottom surface comprises at least one concave arcuate surface, that is, a rounded or curved surface.

The disclosed well plate having a well base having a conical or tapered geometry is superior for injection molding of the well's opaque side wall since it is unnecessary to alter existing flat pins that have been previously used to over-mold on a flat insert (i.e., base). Injection molding with existing flat pins can also be accomplished on a well-bottom geometry having a full radius (i.e., a hemispherical or untapered base). An optional distortion collar feature on the base can enhance the ability of an existing flat pin to achieve shut-off on the well-bottom geometry.

A well plate having the disclosed tapered or chevron shaped (e.g., a 45 degree angle from the sidewall to a radiused apex) well-bottom geometry has been successfully demonstrated for use in the formation of cell spheroids. The tapered well-base or well-bottom geometry also enables over-molding of the opaque well wall onto an insert (base) pre-formed with the tapered geometry using existing flat pins that would ordinarily be used to over-mold on a flat insert. The optional distortion collar feature integral with or attached to the insert (base) can facilitate resin flow shut-off of the injection molding pin. The well-bottom geometry can alternatively be generated by thermal-forming a polymer film prior to over-molding, or after over-molding using a thermal reforming process. Thermal reforming permits rapid change-over to generate well geometries for alternative multiple formats.

The disclosed well plate having a tapered or chevron shaped base (e.g., an approximate 45 degree angle) is advantaged by, for example, permitting over-molding onto the insert using the same pin equipment to over-mold on a flat insert. This over-molding can be facilitated by the addition of a distortion collar that can flex to permit the pin to shut-off the polymer flow. Using the flat pin for molding results in saving time and reducing cost for the generation of this well plate product since the mold-cavity pins do not need to be modified for different well geometries or different well count formats.

Thermal reforming permits rapid change-over to generate well geometries for many different well formats. Thermal reforming also permits design flexibility for assessment of different well geometries for each format and the ability to rapidly produce prototype or production samples for customer evaluation or specification.

A well base having an approximate 45 degree tapered angle also allows for a smaller radiused apex, which apex centers the collection of cells that settle by gravity to form a cell spheroid, and enhances optical imaging.

Figure 4:
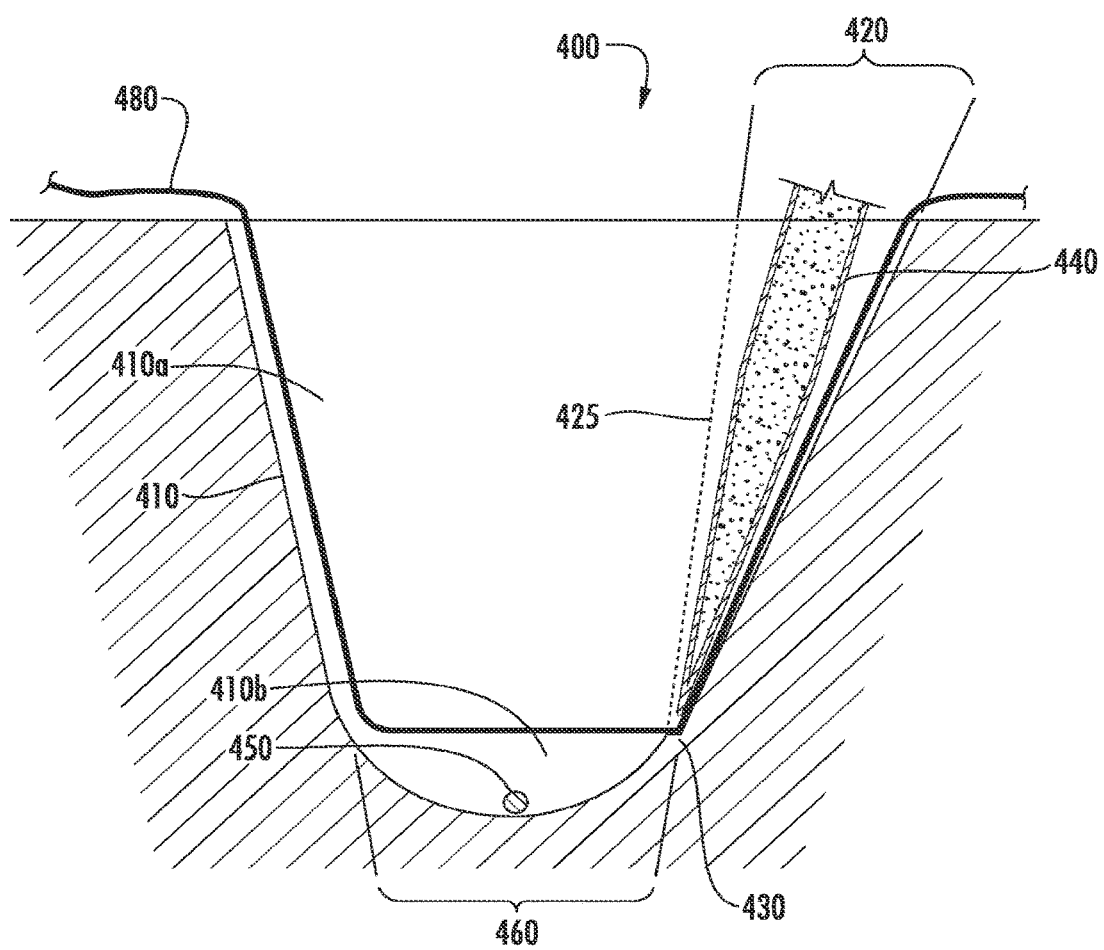
FIG. 4 shows in a cross-section view of a single well or single chamber in the frame of an alternative exemplary article (400).

Referring to the Figures, FIG. 4 shows in a cross-section view an exemplary article (400) having a chamber (410), and a chamber annex (420) for receiving an aspirating pipette (440), and optionally a porous membrane (480), for example, a high throughput screening membrane insert or liner, for dividing the chamber into upper (410a) and lower (410b) chambers, or upper and lower chamber volumes. The chamber annex (420) or chamber extension is not physically separated from the main chamber (410) space, but is instead a spatial extension or expansion of the main chamber. Thus, dotted line (425) represents a non-physical boundary between the main chamber and the chamber annex. The chamber annex and the optional porous membrane provide an excellent geometry that permits aspiration of the medium without aspirating the spheroid (450) mass from the well chamber. The chamber annex (420) having an optional second bottom (430) or stop-ledge provides space to accommodate a pipette tip (440) of a pipette to exchange fluid medium without significantly disturbing the spheroid (450) in the transparent arcuate round bottom surface area and volume (460) of the lower chamber (410b). The stop ledge (430) prevents the pipette tip from entering the lower spheroid chamber.

Figure 5:
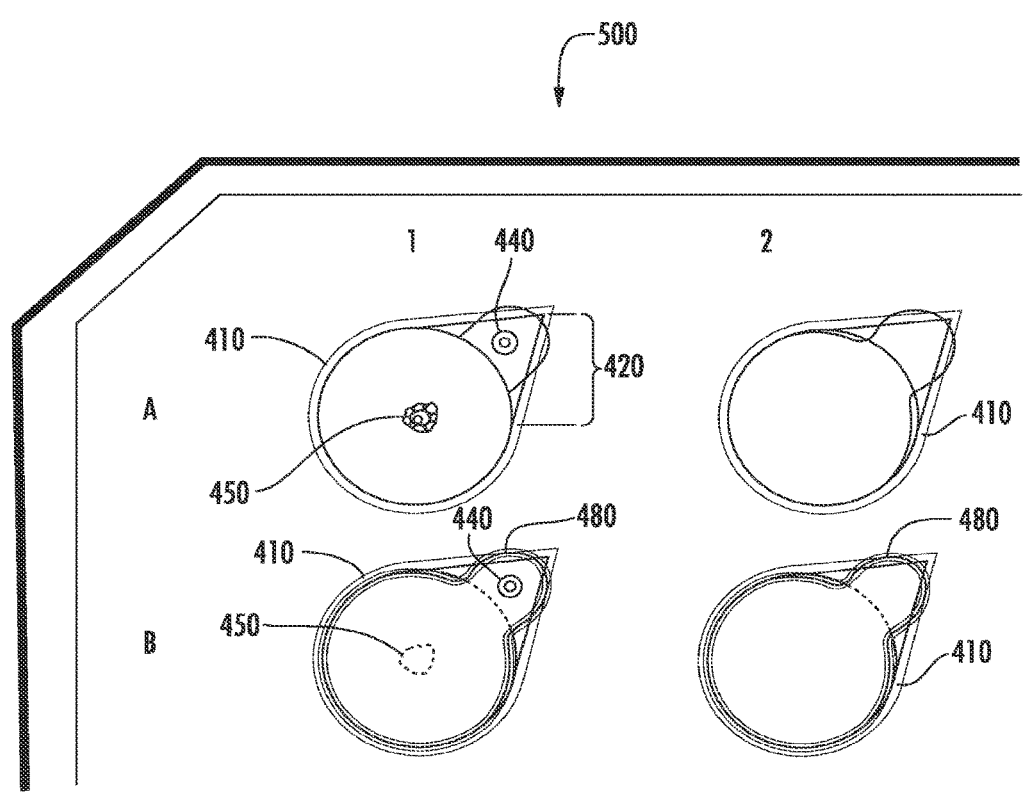
FIG. 5 shows in a partial top or plan view aspects of the exemplary article of FIG. 4.

FIG. 5 shows aspects of the exemplary article of FIG. 4. FIG. 5 shows in the well area A1, a partial top or plan view (500) of the exemplary article of FIG. 4, having a plurality of the chambers (410), each chamber having a chamber annex (420) for receiving the aspirating pipette (440). Additionally or alternatively, FIG. 5 shows in well area B1, the chamber (410) includes the optional porous membrane (480) or liner for dividing the chamber into the upper chamber and the lower chamber (410a and 410b, respectively, not shown) where the porous membrane (480) covers the underlying or hidden spheroid (450). An article having wells configured as shown in area B1 including the porous membrane (480) provide a functioning nested 96-well HTS Transwell® spheroid plate.

Well plates having opaque sidewalls and gas permeable, rounded-bottom wells having clear windows can provide significant advantages including, for example: no need to transfer the spheroid from one multiwell plate (in which spheroids can be formed and visualized) to another plate for conducting assays to, for example, evaluate drug compounds; avoiding the spheroid transfer step can save time and avoid potential loss or disruption of the spheroid; and the spheroids can receive superior oxygenation with well-bottoms made from a polymer having gas permeable properties at a given wall thickness. Increased oxygen availability to the cells in the spheroid culture is particularly helpful for cells with high oxygen requirements such as hepatocytes.

Figure 7:
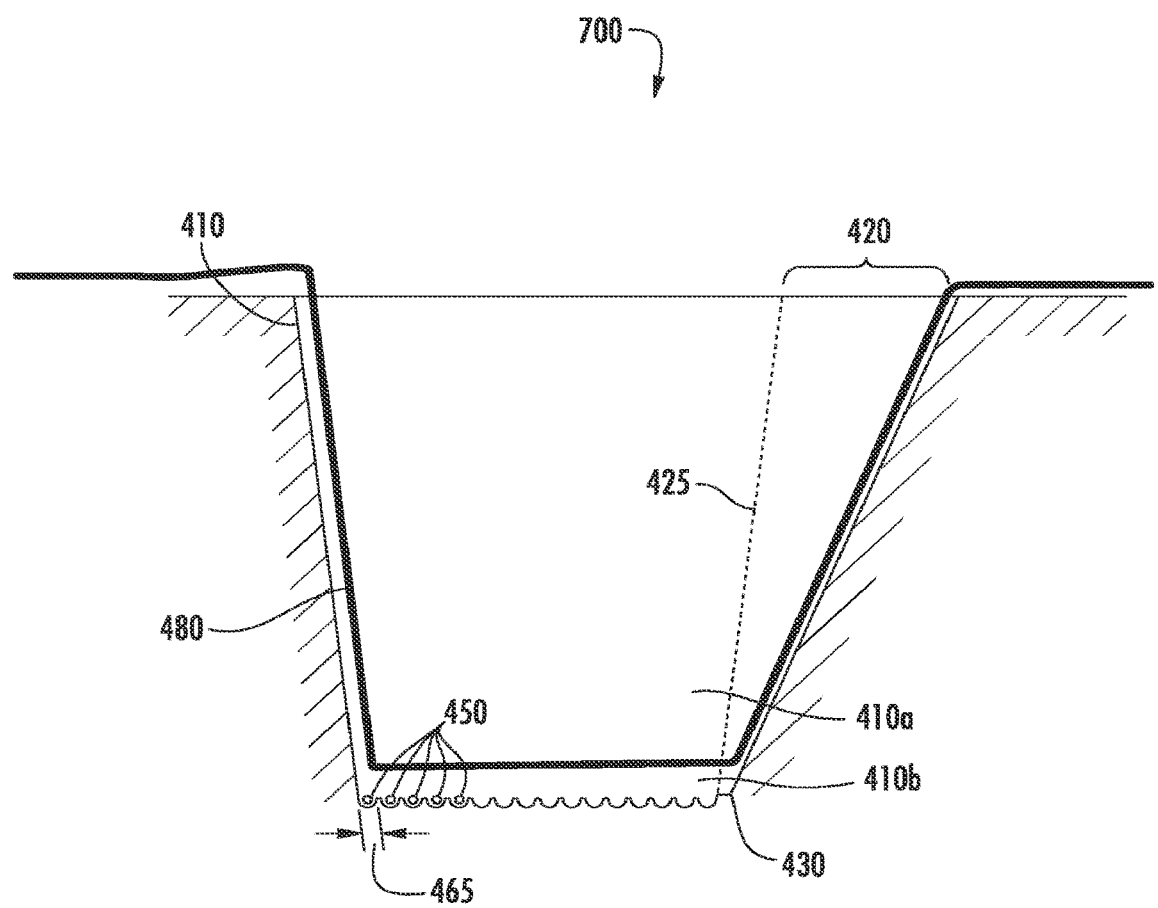
FIG. 7 shows in a cross-section view aspects of an exemplary multi-spheroidal well article (700).
Figure 8:
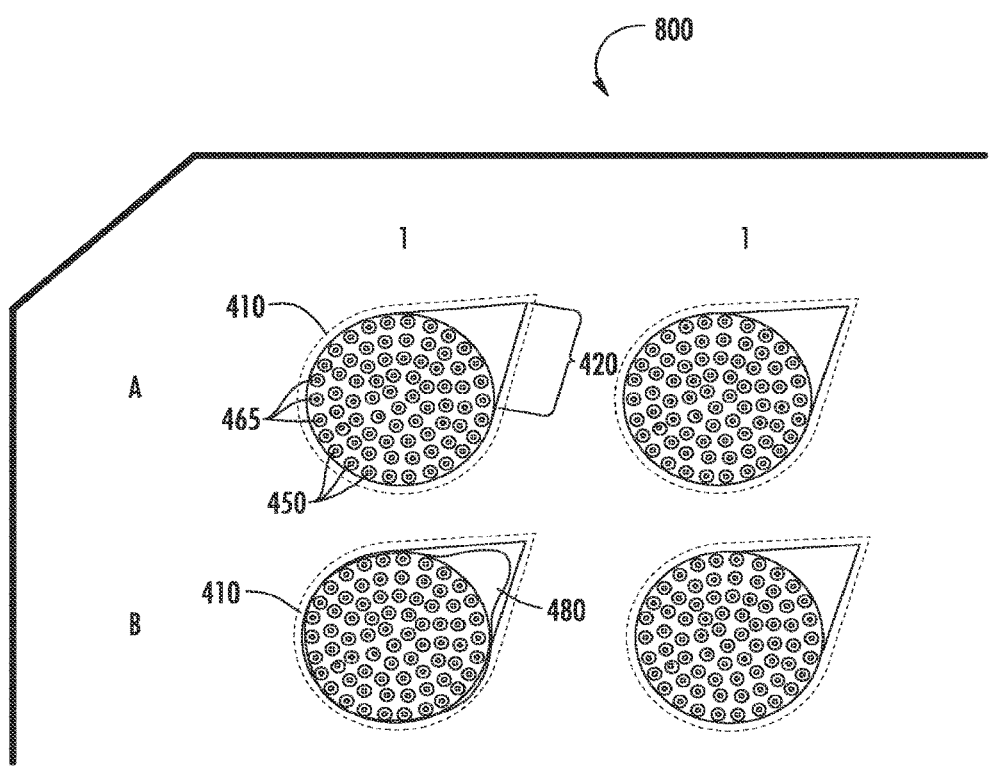
FIG. 8 shows in a partial top or plan view aspects of the exemplary article of the multi-spheroidal well article (700) of FIG. 7.

In embodiments, the article having a chamber having at least one concave arcuate surface can include, for example, a plurality of adjacent concave arcuate surfaces having, for example, from 1 to about 1,000 concave arcuate surfaces on the bottom of the same chamber, see for example, FIGS. 7 and 8.

In embodiments, the article can be, for example, a single well or multi-well plate configuration having numerous "spheroidal wells", such as a plurality of dimples or pits in the bottom or base of each well. The plurality of spheroids or spheroid wells per chamber can preferably accommodate, for example, a single or one spheroid per spheroid well.

In embodiments, the gas permeable, transparent well bottom having the at least one concave arcuate surface or "cup" can be, for example, a hemi-spherical surface, a conical surface having a rounded bottom, and like surface geometries, or a combination thereof. The well and well bottom ultimately terminates, ends, or bottoms-out in a spheroid "friendly" rounded or curved surface, such as a dimple, a pit, and like concave frusto-conicial relief surfaces, or combinations thereof.

In embodiments, the opaque side wall surface (i.e., a surround) can be, for example, a vertical cylinder or shaft, a portion of a vertical conic of decreasing diameter from the chamber top to the chamber bottom, a vertical square shaft or vertical oval shaft having a conical transition, i.e., a square or oval at the top of the well, transitioning to a conic, and ending with a bottom having at least one concave arcuate surface, i.e., rounded or curved, or a combination thereof. Other illustrative geometric examples include holey cylinders, holey conic cylinders, first cylinders then conics, and other like geometries, or combinations thereof.

In embodiments, the article can further comprise, for example, a low-adhesion or no-adhesion coating on a portion of the chamber, such as on the at least one concave arcuate surface.

In embodiments, the article can further comprise, for example, a chamber annex, chamber extension area, or an auxiliary side chamber, for receiving a pipette tip for aspiration, the chamber annex or chamber extension (e.g., a side pocket) can be, for example, an integral surface adjacent to and in fluid communication with the chamber. The chamber annex can have a second bottom spaced away from the gas-permeable, transparent bottom. The chamber annex and the second bottom of the chamber annex can be, for example spaced away from the gas-permeable, transparent bottom such as at a higher elevation or relative altitude. The second bottom of the chamber annex deflects fluid dispensed from a pipette away from the transparent bottom to avoid disrupting or disturbing the spheroid.

In embodiments, the article can further comprise a porous membrane, such as a liner or membrane insert, situated within a portion of the chamber, situated within a portion of the chamber annex, or both the chamber and the chamber annex portion. The porous membrane can provide isolation or separation of a second cellular material, such as a different cell type or different cell state, situated in an upper portion of the chamber, in an upper portion of the chamber formed by the porous membrane, or both chambers, from first cellular material in a lower portion of one or both chambers near the transparent bottom.

In embodiments, the at least one concave arcuate surface can be, for example, a hemisphere, or a portion of a hemisphere, such as a horizontal section or slice of a hemisphere, having a diameter of, for example, from about 250 to about 5,000 microns (i.e., 0.010 to 0.200 inch), including intermediate values and ranges, depending on, for example, the well geometry selected, the number of concave arcuate surfaces within each well, the number of wells in a plate, and like considerations. Other concave arcuate surface can have, for example, parabolic, hyperbolic, chevron, and like cross-section geometries, or combinations thereof.

In embodiments, the spheroid can be, for example, substantially a sphere, having a diameter of, for example, from about 100 to about 500 microns, more preferably from about 150 to about 400 microns, even more preferably from about 150 to about 300 microns, and most preferably from about 200 to about 250 microns, including intermediate values and ranges, depending on, for example, the types of cells in the spheroid. Spheroid diameters can be, for example, from about 200 to about 400 microns, and the upper diameters being constrained by diffusion considerations (for a review of spheroids and spheroid vessels see Achilli, T-M, et. al. *Expert Opin. Biol. Ther*. (2012) 12(10)).

In embodiments, the disclosure provides a perfusion plate apparatus comprising:
at least one cell culture article comprising:
a frame having a chamber, for example, a well, comprising:

an opaque side wall surface;

a top aperture;

a gas-permeable, transparent bottom surface; and optionally a chamber annex surface, the at least a portion of the bottom comprises at least one concave arcuate surface, that is, a rounded or curved surface, media source well in fluid communication with at least one chamber of the cell culture article that controllably provides a source of fresh media to at least one chamber; and a waste well in fluid communication with the at least one chamber of the cell culture article that controllably receives waste media from cell metabolism in the at least one chamber.

Figure 6:
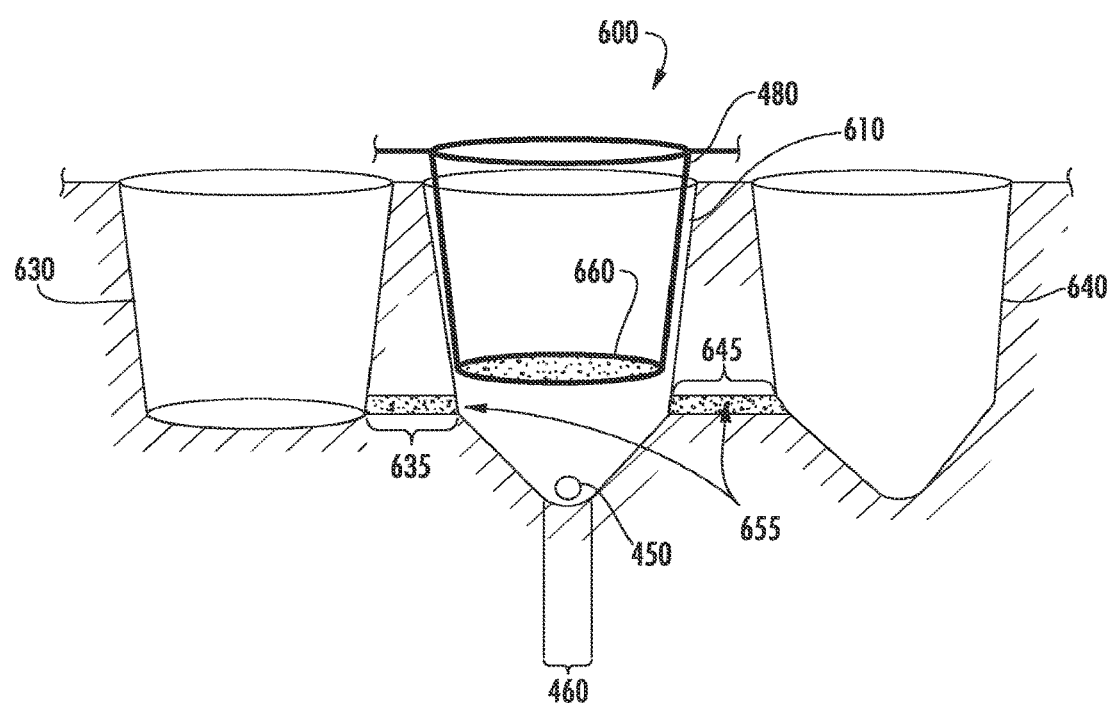
FIG. 6 shows in perspective aspects of an exemplary perfusion plate apparatus (600).

FIG. 6 shows in perspective aspects of an exemplary perfusion plate apparatus (600). In embodiments, the aforementioned perfusion plate apparatus can further comprise a porous liner (480) situated within a portion of the chamber (610), situated within a portion of the chamber annex (not shown), or both the chamber and the chamber annex, the porous liner provides isolation or separation of a second cellular material (660) such as Caco 2 cells, in an upper portion of the chamber, an upper portion of the chamber annex, or both upper portion of the chamber and the chamber annex, from first cellular material, such as a spheroid (450), situated in the lower portion of the chamber or the chamber annex and near the transparent bottom region(460).

In embodiments, the aforementioned perfusion plate apparatus can further comprise, for example: a source liquid (not shown), a perfusion plug (655), i.e., liquid permeable material, situated in a liquid connection member (635), such as a tube, between a source well (630) and the cell culture rounded-bottom well of the apparatus (600), a perfusion plug (655) situated in a liquid connection member (645) between the cell culture rounded-bottom well and the waste well (640), or both situations. The waste well (640) preferably can have an arcuate bottom surface to facilitate removal of waste liquid medium (not shown) using, for example, a pipette, a vacuum pump, or like liquid removal equipment.

A related but distinct cell culture article (i.e., FloWell™ plate) is disclosed in commonly owned and assigned copending application, U.S. Provisional Patent Application Ser. No. 61/594,039, filed on Feb. 2, 2012, now PCT/US13/24030, to Goral, et al., entitled "Automatic continuous perfusion cell culture microplate consumables". The related application mentions, for example, a microplate for culturing cells with automatic, continuous perfusion of a liquid medium, and can include, for example, a well frame which defines a plurality of cavities therethrough. The microplate can further include a planar substrate connected with the well frame. The planar substrate can provide a bottom surface to the plurality of cavities, forming a plurality of wells. The plurality of wells may include a first well, a second well fluidly connected with the first well, and a third well fluidly connected with the first well. The first well may be employed for culturing the cells in the liquid medium. The second well may be employed for providing an outflow or source of the liquid medium to the first well. The third well may be employed for receiving an inflow or waste stream of the liquid medium from the first well. The second well may be fluidly connected with the first well with a first perfusion membrane. A first perfusion membrane can be disposed in between the well frame and the planar substrate and may extend from an outlet section of the second well to an inlet section of the first well. The third well may be fluidly connected with the first well with a second perfusion membrane. The first and second perfusion membranes can have a porosity of, for example, from about 0.2 to about 200 microns. The second perfusion membrane can be disposed in between the well frame and the planar substrate and extend from an outlet section of the first well to an inlet section of the third well. Upon introduction of a perfusion-initiating amount of the liquid medium into the second well, the liquid medium flows from the second well through the first perfusion membrane to the first well and from the first well through the second perfusion membrane to the third well (see for example FIG. 5 therein). The related application also mentions methods of fabricating the microplate and methods of culturing cells.

FIG. 7 shows aspects of an exemplary multi-spheroidal well article (700), which is reminiscent of aspects of FIG. 4 including, for example, one or more chambers (410), each chamber having the chamber annex (420) area bounded by line (425) and stop-ledge (430), for receiving an aspirating pipette (not shown). Unlike FIG. 4, the bottom of each chamber (410) in FIG. 7 can include a plurality of arcuate dimples (465), which dimples can be either or both transparent and gas permeable, and can each receive or cultivate a single spheroid (450). Cells can be seeded into the wells of the apparatus at a low density to permit single spheroid formation and cultivation in the neighboring but separated cups. The multi-spheroidal well article (700) can include the optional porous membrane (480) or liner insert for dividing the chamber into the upper (410a) and the lower (410b) chamber.

FIG. 8 shows aspects of the exemplary article of the multi-spheroidal well article (700) of FIG. 7. FIG. 8 shows, in the well area A1, a top view (800) of the exemplary article of FIG. 7, having a plurality of the chambers (410), each chamber having the chamber annex (420) for receiving the aspirating pipette (not shown). The bottom of each chamber (410) includes a plurality of arcuate dimples (465), which dimpled surfaces can receive or cultivate a plurality of spheroids (450). Additionally or alternatively, FIG. 8 shows, in the well area B1, the chamber (410) includes the optional porous membrane (480) or liner insert for dividing the chamber into the upper chamber and the lower chamber (410a and 410b, respectively, not shown). The membrane (480) or liner insert conceals and protects the underlying spheroids (450) and spheroid wells (465) from disturbances or disruption from forces or activity above the membrane, such as during the addition or removal of liquid medium.

In embodiments, the article having a chamber can include, for example, from 1 to about 2,000 chambers, from 10 to about 1,500 chambers, including intermediate values and ranges, and each chamber is physically separated from any other chamber, and each chamber has a single concave arcuate surface. In embodiments, such a multi-well plate product configuration can have, for example, one spheroid per chamber.

In embodiments, the at least one concave arcuate surface can have, for example, a plurality of adjacent concave arcuate bottom surfaces within the same well. In embodiments, a single well or multi-well plate configuration can have numerous spheroidal wells, such as dimples or pits in the bottom or base of each well. In embodiments, the article can accommodate a plurality of isolated spheroids in separated spheroid wells in a single chamber, preferably having, for example, one spheroid per spheroid well.

In embodiments, the disclosure provides a method of making an article, the article comprising:
a frame having a chamber, for example, a well, comprising:
an opaque side wall surface;
a top aperture;
a gas-permeable, transparent bottom surface; and
optionally a chamber annex surface having a second bottom remote from the transparent bottom surface; and
at least a portion of the transparent bottom comprises at least one concave arcuate surface, that is, a transparent rounded or curved surface;
the method of making comprising:
combining the gas-permeable, transparent arcuate bottom surface portion and an opaque side wall surface portion to form the article.

The method of making the article can further comprise, for example, inserting a porous membrane in at least one of the chambers.

There are several methods that can be used to make an opaque round-bottom multiwell plate having opaque sidewalls and a base with a clear window. The multiwell plate made by Examples 1 or 2, and having flat well bottom geometry can be subsequently thermally-reformed to create an alternative well-bottom geometry. A multiwell plate having a flat well-bottom geometry can be, for example, positioned in a nest that has at each well-bottom position areas removed from the nest that have a circular perimeter in roughly the same dimensions as the well format, or the nest can have a tapered angle, for example, from about 30 to about 60 degrees, including intermediate values and ranges, such as 40 to 50, and 45 degrees, turning into a radius at the apex, that is, rounded at the very bottom of the well. A heated platen, heated for example at 180 to 400 degrees F., more preferably 250 to 300 degrees F., having an array of pins that have, for example, a matching 45 degree tapered angle from the sidewall sloping into a radius at the apex, is held stationary, with a pin positioned over each well. The pin-platen is actuated so that the pins descend into the wells of the multiwell plate to contact the clear flat well-bottom surface. Time, temperature, and pressure can change the well-bottom material geometry as the pins advance until the reformed well-bottom material meets the matching nest geometry. The array of pins may be coated with a release agent, such as PTFE, to prevent the reformed well-bottom geometry from sticking to the heated pins, or the pins can be uncoated. The nest may also have a vacuum assist on the nest to help draw the polymer into the well geometry. Cooling air can be injected into the top of the wells above the heated pins to cool the hot pins slightly and facilitate their release from the polymer of the reformed well-bottom geometry. The platen with the pin array and the nest with the matching geometry can be rapidly changed to comply with many multiple well formats, including 384- and 1536-wells. Any number of wells may be reformed at the same time. In embodiments, the pin-platen can be held stationary while the nest holding the insert can be actuated to be brought into contact with the stationary pin-platen. In embodiments, both the pin-platen and the nest holding the insert can be actuated to provide relative motion that achieves contact and closure between the pins and the wells of the insert.

A v-shaped well base geometry having, for example, a tapered angle of 45 degrees, sloping from the well sidewall to a radius at the apex, is superior for spheroid formation and superior for optical measurement compared to a hemispherical well-bottom geometry. The v-shaped well base geometry also permits overmolding on the well base geometry using the same flat pins that can be used to over-mold opaque polymer onto a flat insert. The 45 degree well base tapered angle permits the pins to contact each well base on the bottom tapered sidewall. While this can also be done with a hemispherical geometry, it is more difficult. If the pin is not able to shut-off on the sidewall, the opaque polymer can leak into or onto the clear well bottom. Alternatively, if the pin cannot achieve shut-off on the sidewall, the pin can be made larger than the well, and achieve shut-off on the flat area surrounding each well at the top of the insert. This alternative solution is not desired because it can create a flat ledge within each well upon which cells can settle. Cells that settle on the ledge cannot contribute to the spheroid in the center of the well bottom, but can cause large variation in experimental results.

In embodiments, the post-forming equipment can have, for example, a heated pin, such as a single pin, a row of pins, or an array of pins, that can match the number and alignment of, for example, a single well or a plurality of wells in a row or an array of wells of an injection molded microwell plate. The geometry at the end of each pin can have, for example, a 45 degree angle or taper from the sidewall and have a radius at or near the apex.

In embodiments, an injection molded plate having a flat well-bottom geometry can be situated and secured in a nest for the post-forming step where the heated pin or pin array assembly is pressed, for example, into the flat well-bottoms of an injection molded microplate. The nest can have a matching 45 degree angle at each well position to match and receive the pin shape. In embodiments, a platen can hold the heated pin or pins and the nest holds the matching well-bottom geometry. The plane of the pin platen and the plane of the nest can be aligned in parallel and both can be perpendicular to a common axis for proper reversible and reproducible pressing.

The platen, the nest, or both, can be rapidly interchanged to accommodate other multiwell plate formats such as 384- and 1536-well plates. The platen bearing the heated pin(s) can be pressed into a matching well(s) of the multiwell plate to form the selected geometry defined by the geometry or cross-section of the pin's tip, such as hemispherical, conical, v-shaped, w-shaped, wedged shaped, and like geometries, or combined geometries, in the clear base of the well.

In embodiments, the disclosure provides a method of culturing spheroids comprising, for example:
charging any of the aforementioned articles with culture media; and
adding spheroid forming cells to the culture media.

Materials and Methods

There are several methods that can be used to make the disclosed article or articles. In embodiments, the disclosed article can be, for example, a multiwell plate having an opaque side wall for the wells and having an arcuate or concave rounded base or bottom surface, the base or bottom surface can be gas permeable and transparent or clear to visible light.

Commonly owned and assigned U.S. Pat. No. 7,674,346, mentions methods of making well plates such as bonding a polymeric holey plate to a glass or polymeric base and using, for example, heat or radiation to weld a gas permeable thin film to a holey plate to form the bottom of microplates (see e.g., col 2, lines 4 to 44).

Commonly owned and assigned U.S. Pat. No. 5,759,494, mentions methods of making well plates having opaque sidewalls by, for example, over-molding inserts to prevent cross-talk. Polymethylpentene (TPX) of the presently disclosed gas permeable spheroid plate can be selected as a suitable base or wall material that can be used in methods of making in the '494 patent and the present disclosure.

In embodiments, the structure of the presently disclosed gas permeable spheroid plate can also include one or more ridges arranged in one or more grid patterns as disclosed in the '494 patent, see for example, col. 4, line 30 to col. 5, line 54, to further reduce or prevent cross-talk. In over-molded plates without a grid, the perimeter of the well, a film, tended to peel away from the molded plate body. The grid appears to keep the film from peeling away from the plate body as it is reforming. The grid also appears to prevent stress marks from appearing in the film, since stress marks do appear in the plates without the grid.

U.S. Pat. No. 6,811,752, mentions methods of making a device having micro-chambers and microfluidic flow, and gas permeable, liquid impermeable membranes.

In one method (insert molding), the multiwell plate bottom or base portion having at least one rounded, cupped, or dimpled impression in the base is injection molded, or thermoformed using a clear polymer. Next, the molded or thermoformed clear multiwell bottom plate is inserted into a vertical press, then an opaque polymer is injected forming the remainder of the multiwell plate onto the clear, round well bottoms. An alternative to insert molding uses a 2-shot molding process.

Referring again to the Figures, FIG. 1 schematically shows methods for joining preformed or molded components. An injection molded or thermoformed opaque, holey plate portion (110) of a multiwell plate (i.e., without well bottoms) is joined to the injection molded or thermoformed clear, round, well-bottom plate portion (120). This joining to form the article (130) can be accomplished by any suitable method, for example, by placing the well-bottom plate (120) (or "insert") into a vertical press and molding the opaque holey plate portion (110) onto the well-bottom plate portion. An alternative method of making can be, for example, injection molding the entire multiwell plate using a 2-shot molding process. The methods form an integral multiwell plate that has clear, rounded-well bottoms and opaque sidewalls. Any method of joinery can be used to attach preformed portions (110) and (120), including, for example, adhesive, ultrasonic, thermal, IR, laser welding, and like methods, or combinations thereof. Subsequent optional well coating with, for example, an ultra-low attachment material, and the force of gravity, can facilitate the cells self-assembling into a spheroid. Using a gas permeable material of appropriate thickness for, at least, the clear, round or cupped well-bottom portion of the multiwell plate enhances oxygen availability for the cells in the spheroid.

EXAMPLE(S)

The following examples serve to more fully describe the manner of using the above-described disclosure, and to further set forth best modes contemplated for carrying out various aspects of the disclosure. These examples do not limit the scope of this disclosure, but rather are presented for illustrative purposes. The working example(s) further describe(s) how to prepare the disclosed cell culture well articles.

Example 1

Injection Mold or Thermoform Methods

Figure 2A:
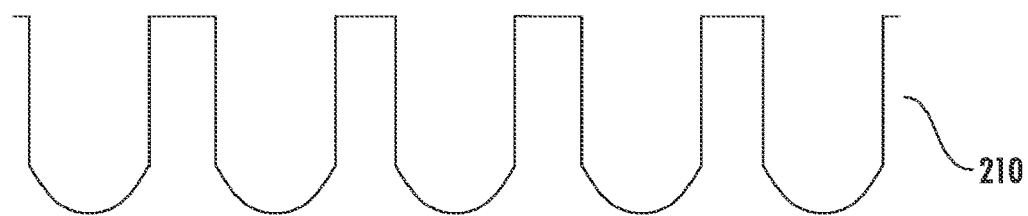
FIGS. 2A to 2C show an alternative method for making a disclosed article having an opaque sleeve or chamber wall surface and a pre-formed clear base insert.
Figure 2B:
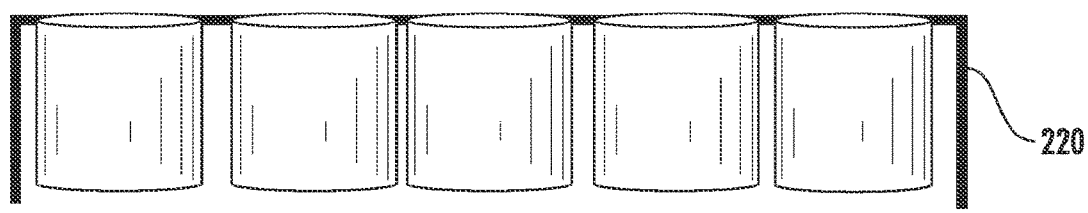
Figure 2C:
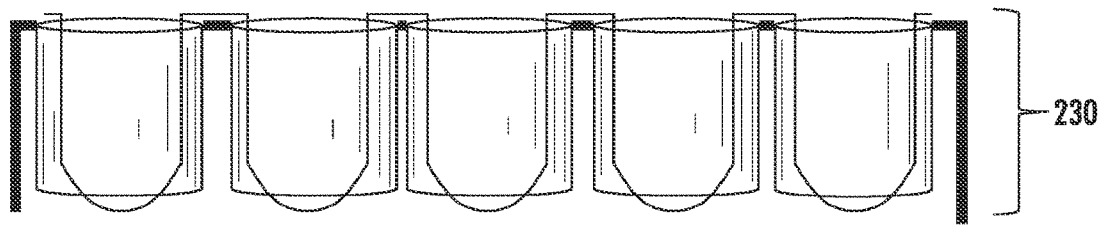

FIGS. 2A to 2C show an alternative method for creating an opaque "sleeve." FIG. 2A shows an injection molded, or thermoformed well portion of a multiwell plate (210) (no skirt) having rounded or cupped well bottoms made using a clear polymer. FIG. 2B shows an injection molded, or thermoformed second multiwell plate including the skirt (220) but without well bottoms made using an opaque polymer. The well diameters of the opaque plate (220) are molded to be slightly larger than the well diameters of the clear plate (210). The clear portion is slipped into the opaque portion and may be permanently attached via a number of suitable methods including, for example, an adhesive, ultrasonic welding, IR welding, thermal welding, laser welding, and like methods. FIG. 2C shows a compression fit of the clear plate into the opaque plate to provide the assembled plate article (230). The opaque plate (220) acts as a sleeve structure to receive the clear plate structure and the combination forms the article having wells having opaque sidewalls and a clear window at the arcuate or rounded base of the well.

Figure 3:
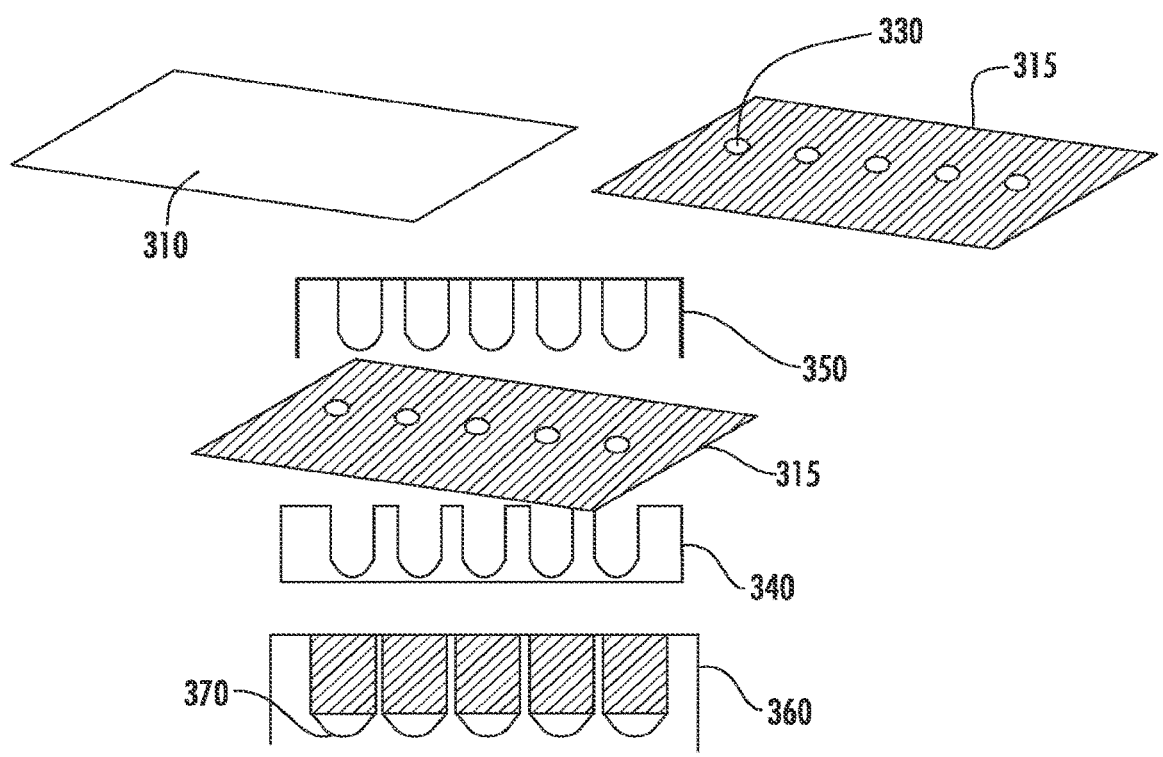
FIG. 3 shows another alternative method of making the disclosed article using distortion printing.

FIG. 3 shows another alternative method of making the disclosed article using distortion printing. A clear polymer sheet (310) is selectively printed with an opaque material to form printed sheet (315) having clear window regions or zones (330). The sheet can be selectively thermoformed to introduce the cups (i.e., the distortion) before or after printing so that the clear zones (330) of the printed sheet (315) become the center of the well bottoms. In embodiments, two halves, for example, a holey plate having clear bottoms (350) and sheet (315) of a mold are used to form the complete multiwell plate (340) from the distortion printed polymer sheet. Once thermoformed into a multiwell plate (360), all of the plate will appear opaque except for the clear zone (370) in the cupped-shaped well bottoms that form a window for optical viewing at or from the well bottom.

Example 2

In another method of making, one can mold or thermoform an opaque multiwell plate that has no well-bottoms (i.e., make an opaque "holey plate"). Next, one can injection mold, or thermoform the multiwell plate bottom or base portion using a clear polymer. Then one can attach the holey plate and base components together using any of various assembly processes, including, for example, adhesive, ultrasonic, IR, thermal, laser welding, and like processes.

Example 3

In another method of making, one can injection mold, or thermoform the entire well of a multiwell plate (without a skirt) using a clear polymer. Next, one can injection mold, or thermoform another multiwell plate (including the skirt) but without well bottoms using an opaque polymer. The well diameters of the opaque plate are molded to be slightly larger than the well diameters of the clear plate. The opaque plate acts as a sleeve to receive the clear plate and thus form opaque sidewalls and with a clear window at the base of the well.

Example 4

In another method of making, one can distortion print an opaque coating on the exterior of a clear polymer sheet, leaving a clear zone in the area that will be thermoformed with, for example, a cup or dimple, or multiples thereof, into the center of the well bottom. Once thermoformed into a multiwell plate, all of the plate will appear opaque except for the clear zone that forms a window for optical viewing.

Example 5

Non-Adhesive Coating

The interior well-bottom surface, walls, or both can optionally be made non-adhesive to cells by coating those surfaces with a polymer that does not have any characteristics that promote cell attachment, such as a perfluorinated polymer, olefin, or like polymers, and mixtures thereof. Alternatively, following assembly of the opaque multiwell plate with clear, round or cupped well-bottoms, the interior well-bottom may be coated with a non-binding material such as an ultra-low attachment material, agarose, nonionic hydrogel, or like materials, that can inhibit cell attachment. Coatings can also be applied to the clear well bottom portion of the multiwell plate prior to joining with the opaque portion. The combination of, for example, a low-attachment substrate, the well curvature in the body and the base portions, and gravity, can induce cells to self-assemble into spheroids, which cell clusters are known to maintain differentiated cell function indicative of a more in-vivo like response (see Messner, et al., *Archives of Toxicology*, Nov. 11, 2012). Perfluorinated polymers or polymers such as poly 4-methylpentene also provide gas permeability at thicknesses normally used in molding processes, which gas permeability can be beneficial for metabolically active cell types. Representative thickness and ranges of gas permeable polymer can be, for example, from about 0.001 inch to about 0.025 inch, from 0.0015 inch to about 0.03 inch, including intermediate values and ranges (where 1 inch=25,400 microns; 0.000039 inches=1 micron). Additionally or alternatively, other materials having high gas permeabilities, such as polydimethylsiloxane polymers, can provide sufficient gas diffusion at a thickness, for example, of up to about 1 inch.

Figures 9A, 9B:
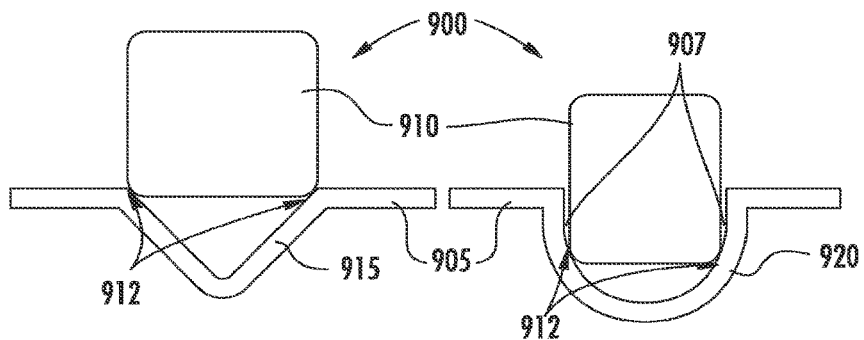
FIGS. 9A and 9B show a cross-section view of the combination (900) of the injection molding pin shut-off in contact with a well-bottom having different geometries.

FIGS. 9A and 9B show a cross-section view of the combination (900) of the injection molding pin shut-off in contact with a well-bottom having different geometries (9A; v-shaped, and 9B; hemisphere shaped). FIG. 9A schematically demonstrates how the pin (910), which fits inside the well, can shut-off (912) on the 45 degree angle of the v-shaped well-bottom geometry (915). FIG. 9B schematically demonstrates how the pin (910) can encounter potential difficulty of achieving shut-off (912) on the hemispherical well-bottom geometry (920).

Figures 10A, 10B:
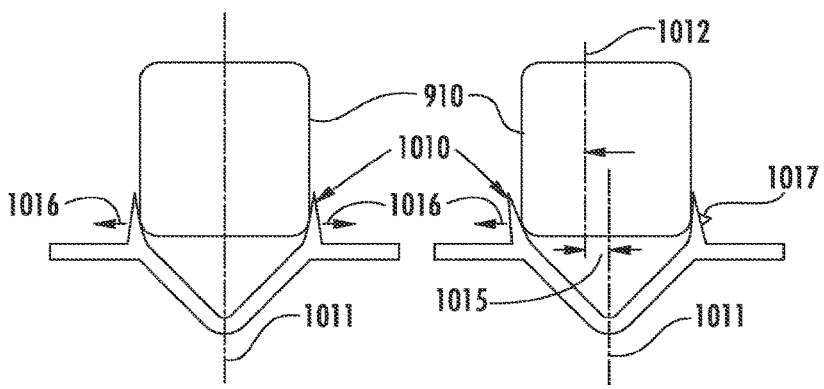
FIGS. 10A and 10B show cross-section views of an alternative design for a pin shut-off.
Figures 11A, 11B, 11C, 11D:
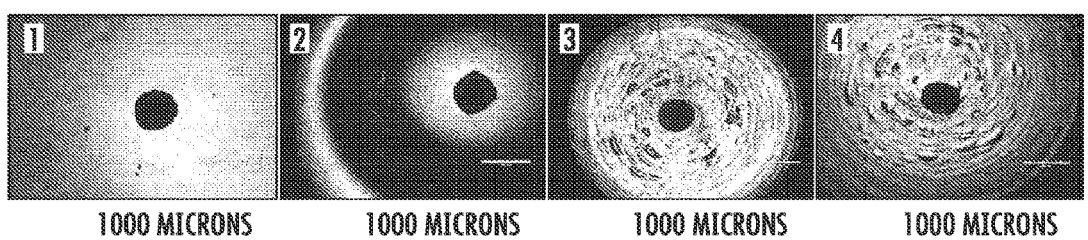
FIGS. 11A to 11D show images of cell spheroids in alternative well-bottoms having different geometries.

FIGS. 10A and 10B show cross-section views of an alternative design for a pin shut-off. FIGS. 10A and 10B demonstrate the utility of an optional distortion collar (1010). The wall thickness of the distortion collar (1010) can be, for example, from about 0.005 to 0.020 inches, and can be determined by, for example, the modulus of the polymer, and the geometric constraints of the multiwell plate. The distortion collar surrounds or brackets the well and is able to distort, i.e., resiliently flex and stretch, under the pressure of the injection molding pin (910) to shut-off, that is, to seal or seal-off the contoured transparent base portion from the injected opaque resin for the side walls. FIG. 10A shows a pin (910) centered in the well and on a common axis (1011) with the pin. FIG. 10B shows the pin slightly offset (1015) from the original common axis (1011) and pin axis (1012), for example as shown, to the left of center. The distortion collar permits the pin to still adequately shut-off or be sealed to prevent the flow of opaque side wall polymer into the clear well-bottom. The distortion collar yields to a greater extent to the left side and yields to a lesser extent on the right side as illustrated by the respective force vector arrows (1016, 1017).

Example 6

Post Forming Method Another method of making a well plate article of the disclosure is accomplished by thermal reforming. In the thermal reforming method a commercially available plate, for example, having standard black (opaque) side-walls and a clear flat plastic bottom is selected. Using a combination of vacuum on the outside and pressure supplied by a hot forming tool with a full radius pushed into the interior of the well(s) on the opposite side of the plate and further into the bottom of the well, the concave arcuate base or tapered base having a round bottom radius is formed in the well bottom. The outside bottom area can be, for example, preheated with IR radiation to facilitate forming the cupped or internal concave arcuate bottom radius, or the tapered base.

Example 7

Method of Use; Culturing of Cells

FIGS. 11A to 11D show images of cell spheroids in different well-bottom geometries. The images were captured on a light microscope at 20× magnification (the reference scale equals 1,000 micrometers).

Image 11A shows a spheroid in an all clear control 96-well plate (i.e., the walls of this comparative plate are transparent) having a full hemisphere well-bottom geometry.

Image 11B shows a spheroid in a prototype thermally reformed 96-well plate having a v-shaped or 45 degree tapered well-bottom geometry.

Image 11C shows a spheroid in an injection-molded single well with the v-shaped or 45 degree well-bottom geometry.

Image 11D shows a spheroid in an injection-molded single well having a full hemisphere well-bottom geometry.

HT-29 cells were seeded into wells including the comparative well (11A) and inventive v-shaped wells (11B and 11C) and hemisphere shaped well (11D) at a concentration of 10,000 cells per well, and incubated for 96 hours at 37 degrees C. in an incubator with 5% $CO_2$ and 85% humidity. The FIGS. 11A to 11D images were captured at 20× magnification on a light microscope after 96 hours of incubation.

The cell seeding procedure generally included the following steps: trypsinize; count the cells; centrifuge to remove medium from the cells; and re-suspend the cells. Seeding densities can be, for example: 10 k, 20 k or 30 k cells per well. The seeding volume can be, for example, 200 microliters per well. Monitoring images can be recorded, for example, at 30 minutes, at 24 hrs, and at 96 hrs after seeding, including intermediate values and ranges.

The spheroids in images 11B and 11C are in the center of the v-shaped well base. The spheroids in images 11A and 11D are not in the center of the hemisphere. The v-shaped base geometry appears to promote centering of the spheroids in the center of the well base, which centering facilitates optical visualization.

In embodiments, one can form a gas permeable, rounded well-bottom using the thermal reforming process. In existing methods, the plates can be molded on flat inserts of, for example, polystyrene that is 0.005", which thickness is considered not gas permeable. However, during the thermal reforming process, one can decrease the thickness of the insert at the radiused apex to, for example, about 0.003"

(photograph not included), which makes the well-bottom as gas permeable as the HYPER-product film (which is also 0.003" thick polystyrene).

The disclosure has been described with reference to various specific embodiments and techniques. However, it should be understood that many variations and modifications are possible while remaining within the scope of the disclosure.

What is claimed is:

1. A cell culture article comprising:
    a chamber comprising:
        an angled side wall;
        a top aperture; and
        a gas-permeable, liquid impermeable bottom comprising at least one concave surface, wherein at least a portion of the bottom is transparent and wherein at least a portion of the bottom comprises a low-adhesion or no-adhesion material in or on the at least one concave surface, wherein the angled side wall has a decreasing diameter from the chamber's top aperture to the bottom; and
    a chamber annex for receiving a pipette tip for aspiration, the chamber annex comprising an integral surface adjacent to and in fluid communication with the chamber, wherein the chamber annex is not physically separated from the chamber, the chamber annex having a second bottom spaced away and at an elevation above the gas-permeable, liquid impermeable bottom, wherein the second bottom deflects fluid dispensed from a pipette away from the gas-permeable, liquid impermeable bottom, and wherein the chamber annex integral surface is angled with the chamber's angled side wall.

2. The article of claim 1 further comprising a liner having a porous membrane situated within a portion of the chamber to divide the chamber into an upper chamber and a lower chamber.

3. The article of claim 1 wherein the article comprises from 1 to about 2,000 of said chamber, wherein each chamber is physically separated from any other chamber.

4. The article of claim 1 wherein the at least one concave surface comprises a plurality of concave surfaces within the same chamber.

5. The article of claim 1 wherein the at least one concave surface comprises a hemi-spherical surface, a conical surface having a taper of 30 to about 60 degrees from the side wall to the bottom, or a combination thereof.

6. The article of claim 1 wherein the side wall surface comprises a vertical cylinder, a portion of a vertical conic of decreasing diameter from the chamber's top to the bottom, a vertical square shaft having a conical transition to the at least one concave bottom, or a combination thereof.

7. The article of claim 1 wherein the at least one concave surface comprises a hemisphere, or a portion thereof, having a diameter of from about 250 to about 5,000 microns.

8. The article of claim 1, further comprising culture media and a spheroid in said chamber.

9. The article of claim 1, wherein said angled side wall is adjacent to the portion of the bottom that is transparent.

10. The article of claim 1, further comprising one or more auxiliary chambers in fluid communication with said chamber.

11. A perfusion plate apparatus comprising:
    at least one cell culture article of claim 1;
    a media source well in fluid communication with the chamber of the at least one cell culture article that controllably provides a source of fresh media to the chamber; and
    a waste well in fluid communication with the chamber that controllably receives waste media from the chamber.

12. The apparatus of claim 11 further comprising a porous liner situated within a portion of the chamber to form an upper chamber and a lower chamber, the porous liner providing separation of a second cellular material in the upper portion of the chamber, from a first cellular material in the lower chamber.

13. The apparatus of claim 11 further comprising: a perfusion plug between the source well and the chamber, a perfusion plug between the chamber and the waste well, or both.

14. The apparatus of claim 11 wherein the at least one concave surface comprises a plurality of adjacent concave arcuate surfaces.

15. A method of making the article of claim 1 comprising:
    combining the gas-permeable, liquid impermeable, bottom and the angled side wall to form the chamber with the top aperture.

16. The method of claim 15 wherein combining is accomplished with: injection molding, thermal reforming, post forming, distortion printing, over molding, or combinations thereof.

17. The method of claim 15 wherein the angled side wall comprises an opaque side wall material, and wherein the chamber includes a distortion collar comprising a wall that surrounds the bottom, wherein the distortion collar is integral with or attached to the bottom, and wherein the distortion collar prevents the opaque side wall material from entering the bottom.

18. The method of claim 15 further comprising inserting a porous membrane in the chamber of the resulting article.

19. A method of culturing spheroids comprising:
    charging the article of claim 1 with culture media; and
    adding spheroid forming cells to the culture media.

20. The method of claim 19 further comprising optically examining the cultured spheroid forming cells through the bottom.

* * * * *